(12) United States Patent
Masaaki et al.

(10) Patent No.: US 7,718,829 B2
(45) Date of Patent: May 18, 2010

(54) PRODUCTION METHOD OF ACROLEIN

(75) Inventors: Okuno Masaaki, Himeji (JP);
Matsunami Etsushige, Himeji (JP);
Takahashi Tsukasa, Himeji (JP);
Kasuga Hiroto, Himeji (JP); Okada Masaki, Suita (JP); Kirishiki Masaru, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 12/227,222

(22) PCT Filed: May 11, 2007

(86) PCT No.: PCT/JP2007/060174

§ 371 (c)(1),
(2), (4) Date: Nov. 12, 2008

(87) PCT Pub. No.: WO2007/132926

PCT Pub. Date: Nov. 22, 2007

(65) Prior Publication Data

US 2009/0177015 A1    Jul. 9, 2009

(30) Foreign Application Priority Data

| May 12, 2006 | (JP) | ............... 2006-134338 |
| May 12, 2006 | (JP) | ............... 2006-134339 |
| Dec. 1, 2006 | (JP) | ............... 2006-325963 |

(51) Int. Cl.
*C07C 45/52* (2006.01)

(52) U.S. Cl. .................... 568/486

(58) Field of Classification Search ............ 568/486
See application file for complete search history.

(56) References Cited

U.S. PATENT DOCUMENTS

| 3,702,886 A | 11/1972 | Argauer et al. |
| 5,387,720 A | 2/1995 | Neher et al. |
| 7,396,962 B1 | 7/2008 | Dubois et al. |
| 2008/0146852 A1 | 6/2008 | Dubois et al. |

FOREIGN PATENT DOCUMENTS

| JP | 6-211724 | 8/1994 |
| JP | 2000-344515 | 12/2000 |
| JP | 2001-58817 | 3/2001 |
| JP | 2001-114512 | 4/2001 |
| JP | 2001-139324 | 5/2001 |
| JP | 2001-180928 | 7/2001 |
| JP | 2006-290815 | 10/2006 |
| WO | 2006/087083 | 8/2006 |

OTHER PUBLICATIONS

International Search Report dated Aug. 21, 2007 in the International (PCT) Application PCT/JP2007/060174.
Dao et al., "Reactions of Model Compounds of Biomass-Pyrolysis Oils over ZSM-5 Zeolite Catalysts", ACS Symposium Series, vol. 376 (Pyrolysis Oils Biomass), pp. 328-341, 1988.

*Primary Examiner*—Sikarl A Witherspoon
(74) *Attorney, Agent, or Firm*—Wenderoth, Lind & Ponack, L.L.P.

(57) ABSTRACT

The present invention has an object to provide a production method of acrolein capable of producing acrolein with suppressing the yield change with time. The production method of the invention is that glycerin is dehydrated under coexistence with a catalyst having crystalline metallosilicates containing at least one kind of T atoms and 15% by mass or less of a binder, and the Si atoms to T atoms ratio (Si/T) of the catalyst is 800 or less.

15 Claims, No Drawings

PRODUCTION METHOD OF ACROLEIN

BACKGROUND OF THE INVENTION

1. Field of the Invention

The present invention relates to a method for producing acrolein by intramolecular dehydration reaction of glycerin.

2. Description of the Related Art

Bio diesel fuels produced from vegetable oils draw attentions not only as an alternative fuel of fossil fuels but also as a point of low emission of carbon dioxide, and the increase in demand is expected. Since glycerin is generated as a by-product in producing this bio diesel fuels, it is necessary to utilize the by-product. As an embodiment of use of glycerin, it can be listed that glycerin is used as a raw material for acrolein.

Production methods of acrolein using glycerin as its raw material have been already disclosed in publications.

For example, in Japanese Unexamined Patent Publication No. Hei 06-211724 (1994), there is disclosed a production of acrolein such that glycerin is dehydrated using H-ZSM-5 of MFI type zeolite having an acid strength function $H_0$ of +2 or less. However, in the case of production of acrolein in gas phase dehydration reaction of glycerin, there is a description in the above patent publication that it is not suitable to use a catalyst with a $H_0$ value of −8.0 or less, and in examples of the above patent publication, there is a description that reactivity of catalyst was markedly lowered in continuous use of catalyst in examples of the above patent publication.

Further, in the specification of International Publication No. WO2006-087083, there is disclosed (1) a production method of acrolein by gas phase dehydration reaction of glycerin that a catalyst prepared by mixing H-ZSM-5 of a range of $-10<H_0<-16$ and Aerosil was used; (2) conversion rate of glycerin and yield of acrolein were lowered with passage of time.

Besides, in Le H. Dao, Reaction of Model Compounds of Biomass-Pyrolysis Oils Over ZSM-5 Zeolite Catalysts, American Chemical Society, 1988, 376, p. 328-341, it is disclosed that gas phase dehydration of glycerin was conducted using a catalyst. It is described that the catalyst used herein was composed of bentonite of 20% by mass and H-ZSM-5 of 80% by mass, and the H-ZSM-5 contained $Na_2O$ of 0.55% by mass.

As disclosed in the above publications, acrolein can be produced by dehydration of glycerin using a catalyst. In the case where yield change of acrolein with time in the production are not so large, the production plan can be easily designed, thus short or excess of the production amount of acrolein may be prevented. Further, when acrolein can be produced with a high yield, it is expected that acrolein derivatives, such as acrylic acid, 1,3-propanediol, ally alcohol, polyacrylic acid, polyacrylate and methionine, which are conventionally known to be produced from acrolein as a raw material, can be produced with low costs.

DISCLOSURE OF THE INVENTION

In the light of the above situations, the present invention has an object to provide a production method of acrolein capable of producing acrolein while suppressing yield change with time.

The present inventors have found the following and accomplished the present invention: yield change of acrolein with time can be lowered when acrolein is produced using acidic crystalline metallosilicates as a catalyst having a Si/T ratio in a specific range and restricted amount of a binder therefor.

The present invention is a production method of acrolein by dehydrating glycerin under coexistence with a catalyst having crystalline metallosilicates containing at least one kind of T atoms, wherein the amount of a binder in the catalyst is 15% by mass or less, and a Si/T ratio in the crystalline metallosilicates is 800 or less.

According to the present invention, by using the crystalline metallosilicates as the catalyst, the Si/T ratio of the crystalline metallosilicates is in the specific range and the upper limit of the binder is set, acrolein can be produced while suppressing yield change of acrolein.

DESCRIPTION OF THE PREFERRED EMBODIMENTS

The production method of acrolein of the present invention will be described below with reference to embodiments. The present method is a method for producing acrolein by dehydrating glycerin under coexistence of a catalyst for dehydration of glycerin. Hereinafter "catalyst for dehydration of glycerin" is simply referred to as "catalyst".

The above catalyst has crystalline metallosilicates. Generally, the size of the catalyst is preferably about 0.1 to 10 mm in corresponding diameter; the shape, which can be spherical, columnar, ring- or saddle-shaped etc., is not particularly limited.

When the dehydration reaction of glycerin is conducted in an industrial scale using the catalyst, there is a case of using a compact of the crystalline metallosilicates as the catalyst. As the catalyst in this case, there can be used the compact composed of a binder and the crystalline metallosilicates, or of the crystalline metallosilicates alone. In the case where a material of the compact as the catalyst has the binder, the amount of the binder and the yield variation of acrolein with time are correlated, and the amount of the binder in the catalyst is preferably 15% by mass or less. Since the lower the amount of the binder, the more the yield variation of acrolein is suppressed, the amount of the binder is more preferably 10% by mass or less, and further preferably 5% by mass or less. The optimum amount of the binder is 0% by mass. The best is the compact of the catalyst with none of the binder, diluting the catalyst reactivities of the crystalline metallosilicates.

Herein, the term "binder" contained in the catalyst refers to a sintering inorganic compound which presents between adjacent metallosilicate crystals. As preferred binders in the present embodiments, for example, there are inorganic sintering oxides such as silica, alumina and titania; and clay minerals such as bentonite and active white earth. Additionally, when a clay mineral is to be the binder, it sometimes includes one or more kinds of cations belonging to alkali metals and alkaline earth metals in its composition. In the case of including the alkali metal cations, the mole amount of the ion-exchanging sites of crystalline metallosilicates is required to be more than the mole amount of cations contained in the clay mineral (½ fold mole amount of the amount number contained in the case of alkaline earth metal cations); and it is not preferable when the mole amount of the ion-exchanging sites of the crystalline metallosilicates is less than that of the cations contained in the clay mineral because the excess cations will disturb dehydration reaction of glycerin.

The crystalline metallosilicate in the present embodiments is a crystal constituted with $SiO_4$ and $TO_4$ of regular tetrahedron structure as a basic constitutional unit, these $SiO_4$ and $TO_4$ are connected three-dimentionally. As the crystalline metallosilicate in the catalyst of the present embodiments, there can be listed: a metallosilicate with a crystal structure classified in structural codes provided by International Zeolite Society Structure Committee, and a metallosilicate with a structures described in "ZEOLITES, Vol. 12, No. 5, 1992" and "HANDBOOK OF MOLECULAR SIEVES, edited by R. Szostak, published by VAN NOST RAND REINHOLD"; the crystal structure is not particularly limited. When the crystalline metallosilicate is exemplified on the basis of denomination according to International Zeolite Society Structure Committee, it is to be a crystalline metallosilicate of 8-membered oxygen ring of pore entrance such as LTA, CHA, ERI and KFI; a crystalline metallosilicate of 10-membered oxygen ring of pore entrance such as FER, MEL, MWW and MFI; and a crystalline metallosilicate of 12-membered oxygen ring of pore entrance such as MOR, BEA, FAU, LTL, GME, OFF and MTW. Among the exemplified crystalline metallosilicates, from the point of acrolein production with high yield, a crystalline metallosilicate with the crystal structure of MEL, MWW, MFI or BEA is preferable, particularly preferable is the crystalline metallosilicate with the crystal structure of MFI.

T atoms in constitutional unit. $TO_4$ of the crystalline metallosilicates are atoms other than Si, and there are listed one or more selected from Al, B, Ti, Cr, Fe, Co, Ni, Cu, Zn, Ga, In, P, Sc, V, Ge, As, Y, Zr, In, Sn, Sb, and La. From the point of the catalyst reactivity and its easiness of production, the T atoms are preferably selected from Al, B, Fe, Ga, In, Co, Ni, and Zn. In the case of being selected from Fe, Ga and Al, it is preferable because acrolein can be produced in high yield, and the case of Al being selected therefrom is particularly preferable.

Mole ratio Si/T of Si atoms to T atoms in the crystalline metallosilicates is 800 or less. When the Si/T exceeds 800, yield change of acrolein with time will be large, or yield of acrolein will become extremely low. Further, preferable Si/T for suppressing yield change of acrolein with time is 10 to 600. Moreover, preferable Si/T for producing acrolein with a high yield is 10 to 400; 20 to 300 is further preferable.

The content of T atoms not incorporated in the crystal lattices of the crystalline metallosilicates (hereinafter "T atoms not incorporated in the crystal lattices of the crystalline metallosilicates" are sometimes referred to as "heteroatoms outside of the crystal lattices") preferably has a certain limitation. It is because when thermal stability of the crystalline metallosilicates with same Si/T is compared in the cases of presence and absence of the heteroatoms outside of the crystal lattices, wherein the crystalline metallosilicates having the heteroatoms outside of the crystal lattices is present may be thermally unstable and essentially less in the amount of catalyst reactive sites. The content of the heteroatoms outside of the crystal lattices of the crystalline metallosilicates relative to the whole T atoms in the catalyst, for example when T atoms are Al, is preferably 3% by mass or less, more preferably 2% by mass or less, and further preferable to be undetectable with analytical equipments (substantially not contained). The content of aluminum atoms outside of the crystal lattices can be calculated by measuring, using $^{27}Al$ MAS-NMR, the aluminum atoms outside of the crystal lattices that usually six-coordinated oxygen atoms and aluminum atoms inside of the crystal lattices that four-coordinated oxygen atoms. Namely, the area of peak measured in a range of $\sigma=50$ to 70 ppm attributed to four-coordinated aluminum and the area of peak measured in a range of $a=0$ to 10 ppm attributed to six-coordinated aluminum are calculated, the content of aluminum atoms outside of the crystal lattices can be determined on the basis of the area ratio of two peak areas.

Each of the crystalline metallosilicates has a first pore, the diameter of the first pore is primary pore diameter. Catalyst reactivity generally depends on the primary pore diameter, however yield of acrolein is hardly affected by the size of the primary pore diameter. Hence, the primary pore diameter in the catalyst in the present embodiments is not particularly limited.

On the other hand, a second pore is between the crystalline metallosilicates, the diameter of the second pore is secondary pore diameter. This diameter is preferably 0.80 μm or less to obtain acrolein in high yield, further preferably in 0.05 to 0.80 μm. Herein, the secondary pore diameter is value defined by mode diameter on volume basis of pore distribution measured in a mercury injection method, at a measuring pressure of 1 to 60000 psia, contact angle of 130°, given that the surface tension of mercury is 485.0 mN/m and density of mercury is 13.5335 g/cm$^3$. Further, to suppress change of acrolein yield, the secondary pore diameter defined by the above mode diameter is preferably 0.08 to 0.40 μm, further preferably 0.10 to 0.25 μm.

Specific surface area of the catalyst is not particularly limited, but when it is measured by nitrogen absorption according to a BET method, 300 to 550 m$^2$/g is good, and 315 to 500 m$^2$/g is preferred.

Degree of the crystallinity of the crystalline metallosilicate is preferably 85% or more, more preferably 95% or more, and further preferably 98% or more.

The crystalline metallosilicate has ion-exchangeable cations outside of the crystal lattices thereof. As the ion-exchangeable cation in the present embodiments, there can be exemplified $H^+$, $Li^+$, $Na^+$, $Rb^+$, $Cs^+$, $Mg^{2+}$, $Ca^{2+}$, $Sr^{2+}$, $Ba^{2+}$, $Sc^{3+}$, $Y^{3+}$, and $La^{3+}$. From the point of high yield of acrolein, H-crystalline metallosilicate with $H^+$ in a part or total of the ion-exchangeable cations outside of the crystal lattices is particularly preferable. In L atom is an ion-exchangeable cation outside of the crystal lattice other than H derived from a raw material for the crystalline metallosilicate synthesis, mole ratio L/T of the L atoms to the T atoms in the crystalline metallosilicates is less than 0.3 will be useful for an intermediate of catalyst production in the third method described later. L/T is calculated from analytical value using a fluorescent X-ray analyzer.

In the case where L atoms contained in the crystalline metallosilicates are Na atoms, since a large content of the Na atoms lowers the yield of acrolein, the content of Na in terms of $Na_2O$ in the crystalline metallosilicates may be suitably 1.0% by mass or less, preferably 0.1% or less, more preferably 0.05% by mass or less, further preferably 0.010% by mass or less, and most preferably 0.005% by mass or less. The Na content in terms of $Na_2O$ in the crystalline metallosilicates is a value calculated from analytical values using a fluorescent X-ray analyzer.

Additionally, in the case where the catalyst contains the binder, Na atoms are sometimes included in the binder. In all of the catalyst of this case, Na content in terms of $Na_2O$ is preferably 1.0% by mass or less from the point of enhancing yield of acrolein, more preferably 0.05% by mass or less, and further preferably 0.01% by mass or less. It is preferable to add at least one kind of M atoms to crystalline metallosilicates having the above-described L/T of 0.3 or less. The M atoms are atoms selected from alkali metal atoms, alkaline earth metal atoms and rare earth metal atoms. The catalyst containing the crystalline metallosilicates to which M atoms are added can produce acrolein in high yield even when concentration of glycerin as raw material of acrolein is high, and has low deterioration of its catalyst reactivity. Further, there is a relatively low amount of coke adhering on the surface of the catalyst, so it is possible to lower the burning temperature of coke adhering on the surface of the catalyst to refine the catalyst. The following can be considered as reasons for achievements of high yield of acrolein: the suppression of deterioration in catalyst reactivity, and the reducing effect on the amount of coke. Strength of the reactive point of the catalyst, its position and distribution may affect the amount of the coke generation. The coke generation is remarkably accelerated when the catalyst have a lot of high reactive points, so that reactivity of the catalyst may rapidly be deteriorated. However, the crystalline metallosilicates to which M atoms are added are suitably adjusted in the strength and distribution of reactivity as the catalyst; as a result, it is thought that the amount of the coke generation and the deterioration of the catalyst reactivity are suppressed while suppressing the lowering of acrolein yield.

Regarding L/T, L/T<0.2 is good; L/T<0.1 is preferable; L/T<0.05 is more preferable; L/T<0.01 is further preferable, and the best is that almost all of L atoms are replaced with protons. "Almost all of L atoms are replaced with protons" means that L/T is zero (below detection limit).

It is preferable that the mole amount of the above L atoms, the mole amount of the above M atoms and the mole amount of the above T atoms satisfy 0<(L+M)/T<1.0. In this case, the effect that M atoms are added to crystalline metallosilicates of the above L/T<0.3 is further improved. Additionally, L/T necessary for determining the value of (L+M)/T is calculated from analytical values using a fluorescent X-ray analyzer as described above. On the other hand, M/T is calculated by the mole amount of T atoms in compound of T atom source used for preparation of the crystalline metallosilicates and the mole amount of M atoms in compound of M atom source used for adding M atoms to crystalline metallosilicates.

The above M atoms are preferably at least one kind selected from Li, Na, K, Rb, Cs, Ca, Sr, Ba, Y, La and Ce.

Next, production methods of the catalyst in the present embodiments will be described on the basis of first production method, second production method, and third method.

First, the production method of the catalyst in the present embodiments will be described on the basis of the first production method.

The first production method is a method for preparing crystalline metallosilicates compact by adding a binder to particles of the crystalline metallosilicate. The method is a simple one that the particles are bonded with the binder to form into an intended shape. In this method, a commercially available particle of the crystalline metallosilicate, a particle of the crystalline metallosilicate which synthesized in known methods such as hydrothermal synthesis method, or a particle of the crystalline metallosilicate which produced in the second production method described below may be suitably used. Further for the binder, inorganic binders such as silica and alumina may be suitably used.

Next, the production method of a catalyst in the present embodiments will be described on the basis of the second production method that a crystalline metallosilicates compact is prepared without adding a binder. Additionally, the major difference between the first method and second production method is that the binder is or is not added in the production process.

"Binder is not added" in the second production method means no addition of a binder after preparation of crystalline metallosilicates. The second production method is a method for producing metallosilicate having a very small diameter of a crystal particle and MFI structure with high catalyst reactivity. The second production method includes a carrying step for carrying an predetermined component on silica compact, crystallization step for contacting the compact after the carrying step with water vapor to synthesize metallosilicate with MFI structure, ion-exchanging step for producing $NH_4$-MFI metallosilicate, and burning step for producing H-MFI metallosilicate. This production method will be described below in each step.

In the carrying step, a silica compact is impregnated in an aqueous solution containing predetermined component (hereinafter referred to as "impregnation liquid"), then the silica compact is dried, thereby to produce metallosilicate precursor.

The silica compact used in the carrying step is not particularly limited. Commercially available silica compacts may be used. The shape and size of the compact are also not particularly limited. As the shape of the compact, spherical, cylinder type and ring type are exemplified. The size is ordinarily 0.5 to 10 mm in a corresponding diameter.

Moreover, mechanical strength of the silica compact is not particularly limited; it is suitably 9.8 N or more in an average of measurements for ten pieces of silica compacts using a Kiya-type hardness tester, preferably 9.8 to 490 N. Since the mechanical strength of the silica compact is correlated with the mechanical strength of the catalyst to be produced, by using the silica compact with high mechanical strength, it is possible to produce the catalyst with a workable strength in a practical use.

The impregnation liquid contains one kind to three kinds selected from T atom component, tetraalkylammonium component, and alkali metal component. The content of the one kind to three kinds contained in the impregnation liquid is suitably set according to the amount to be carried on the silica compact.

In the case where the T atom component is contained in the impregnation liquid, there may be suitably the T atom component containing at least one kind selected from Al, B, Ti, Cu, In, Cr, Fe, Co, Ni, Zn, Ga, P, Sc, V, Ge, As, Y, Zr, Sn, Sb and La. For example, when producing aluminosilicate wherein T atoms are aluminum, it is preferable that Al atom containing compound such as aluminate, aluminum nitrate, aluminum sulfate, halogenated aluminum and aluminum hydroxide, and sodium aluminate is used as the T atom component. Further, when producing metallosilicate containing B, Ti, Cu, In, Cr, Fe, Co, Ni, Zn, or Ga as T atoms, it is preferable that boric acid, titanium chloride, cupper nitrate, indium nitrate, chromium nitrate, iron nitrate, cobalt nitrate, nickel nitrate, zinc nitrate, or gallium nitrate is used as the T atom component.

The amount of the T atom component in the impregnation liquid is set according to a Si/T ratio of crystalline metallosilicates.

Further, when the tetraalkylammonium component is contained in the impregnation liquid, for example, there may be suitably used halogenide or hydroxide such as tetramethylammonium, tetraethylammonium, tetra-n-propylammonim, tetraisopropylammonium, tetra-n-butylammonium, tetra-n-pentylammonium, triethylmethylammonium, triethyl-n-propylammonium, tri-n-propylmethyl ammonium, tri-n-butylmethylammonium. To efficiently synthesize aluminosilicate with MFI structure, a tetraalkylammonium compound having tetraalkylammonium with an alkyl group of 1 to 5 carbon numbers in the constitution is preferably used, a tetraalkylammonium compound having tetra-n-propylammonium in the constitution is more preferably used, and use of tetra-n-propylammonium hydroxide is most suitable.

Further, when the alkali component is contained in the impregnation liquid, hydroxides or halogenides of lithium, sodium and potassium may be contained in the impregnation liquid. When a sodium component is contained, sodium aluminate, which can become the T atom component as well, is preferably contained.

When the impregnation liquid is impregnated into the silica compact, all of the T atom component, the tetraalkylammonium component and alkali metal component are impregnated and carried in the silica compact. When the impregnation liquid contains one kind or two kinds of the T atom component, the tetraalkylammonium component and the alkali metal component, the impregnation operation can be divided into plural steps to carry all of the T atom component, the tetraalkylammonium component and the alkali metal component may be carried in the silica compact. In the case where the T atom component and the other ones are carried in such plural steps, there is no influence on the catalyst to be produced by the order of carrying the T atom component and the other ones.

The total amount of the impregnation liquid to be impregnated into the silica compact may be set according to the corresponding amount that the silica compact can absorb water.

Further, when impregnation operation is divided into plural steps, the each amount of respective impregnation liquids may be set according to the amount that the silica compact can absorb.

Regarding the drying of the silica compact after the impregnation, it may be conducted under vacuum or normal pressure, or may be conducted under air stream at normal pressure. In drying the silica compact, to suppress elusion of the component carried in the next step of crystallization step, it is suitable to dry so that water content of the silica compact comes to 30% by mass or less, preferably to 0.1 to 20% by mass. In this case drying temperature is suitably in a range of 20 to 120° C. where the decomposition of the tetraalkylammonium is little, preferably 50° C. or higher.

Regarding the drying time of the silica compact, the mode diameter of the crystalline metallosilicates will become shorter with longer drying time, the mode diameter of the crystalline metallosilicates compact will become longer with shorter drying time; thus, the drying time is appropriately set according to the any mode diameter. For example, in the case where the drying is conducted at 80° C., the drying time is set to be 7 hours when the mode diameter is set to about 0.07 to 0.08 μm, the drying time is set to be 5 hours when the mode diameter is set to about 0.10 to 0.20 μm, the drying time is set to be 3 hours when mode diameter is set to about 0.50 μm, and the drying time is set to be 0.5 hours when the mode diameter is set to about 0.90 μm.

The metallosilicate precursor is obtained by drying the silica compact. Since the metallosilicate precursor is the silica compact wherein the impregnation liquid is contained, followed by being dried, the T atoms component, tetraalkylammonium component and alkali metal component are carried homogenously therein.

The T atom components and the other ones are carried in the dry silica compact. This compact is the metallosilcate precursor. The composition of the precursor is expressed by the following formula (1):

$$Si_1TxLy(SDA)z \quad (1)$$

in the formula (1), L is alkali metal; SDA is tetraalkylammonium, x is 0.00125 or more (preferably 0.00167 to 0.1, more preferably 0.0025 to 0.1, further preferably 0.0033 to 0.05); y is 0.0001 to 1 (preferably 0.0005 to 0.5); and z is 0.001 to 1 (preferably 0.002 to 1, further preferably 0.003 to 0.8). Herein, when the composition ratio y of alkali metal L is too low, hydrolysis of silica is insufficient, and the conversion into the crystalline metallosilicate will become difficult in the crystallization step; whereas when the composition ratio y of alkali metal L is too large, the hydrolysis of silica will proceed too much, and the silica compact will dissolve. Hence, the numerical range of y is as described above. Further, when the composition ratio z of tetraalkylammonium (SDA) is too low, the silica hydrolyzed in the crystallization step will become difficult into the formation of the crystalline metallosilicate, whereas when the composition ratio z of tetraalkylammonium (SDA) is too large, the impregnation liquid will become high viscosity, which may cause difficulty in the formation of the crystalline metallosilicate, as well as tetraalkylammonium is wasted. Hence, the numerical range of z is as described above.

The crystallization step is conducted in such a way that the metallosilicate precursor contacts saturated water vapor. In the crystallization step, the heat of water vapor condensation in the pore of the precursor promotes the hydrolysis of the silica, the silica crystal containing aluminum is formed in the periphery of SDA, thereby the metallosilicate precursor is converted into MFI. The present crystallization step differs from an ordinary hydrothermal synthesis method as production method of a metallosilicate; it is the step that the metallosilicate precursor is placed in the saturated water vapor, thus the metallosilicate in MFI crystal structure can be synthesized while maintaining the shape of the metallosilicate precursor and suppressing the elusion of Si and T atoms from the metallosilicate precursor.

In the crystallization step as described above, the saturated water vapor is contacted with the metallosilicate precursor. As this contacting method, for example, there are methods: (1) the metallosilicate precursor is placed in a pressure-resistant container apart from the bottom part thereof, and after introducing a certain amount of water, corresponding to the certain amount of saturated water vapor determined by both of the temperature and the volume of the container, then the pressure-resistant container sealed is heated in a constant temperature bath; (2) using a double container constructed with an inner and an outer containers, the metallosilicate precursor is placed in the inner container, and water is put in the outer container, and then the double container is sealed and heated so that the metallosilicate precursor is contacted with water vapor; and (3) a moving bed method wherein the metallosilicate precursor is continuously fed into saturated water vapor.

The temperature in the crystallization step is not particularly limited as long as it is the temperature where the metallosilicate precursor can be converted into MFI, and it is suitably 80 to 260° C. which causes less decomposition of tetraalkylammonium carried in the precursor and is able to produce MFI with high crystallinity. The preferable temperature is in the range of 100 to 230° C. The time for which the metallosilicate precursor is contacted with saturated water vapor is preferably 2 hours or more to promote the crystallization sufficiently. The upper limit of the time is preferably within 150 hours to suppress mixed crystals with crystals other than MFI.

The metallosilicate of MFI structure obtained through the crystallization step will ordinarily become the crystalline metallosilicate with a degree of crystallization of 85% or more in the above-described temperature and time of the crystallization step. In the above crystallization step, it is also possible to produce the crystalline metallosilicate with a degree of the crystallization of 98% or more by adjusting the temperature and time. In this case, the degree of crystallization will become higher with a longer contacting time with saturated water vapor, and, reversely, the degree of the crystallization will become lower with a shorter time, so the degree of the crystallization can be any degree of crystallization. Hence, by lengthening the contacting time with saturated water vapor, it is possible to produce the crystalline metallosilicate with the degree of crystallization of 100% having substantially no binder.

In the ion-exchanging step, L atom in a L-crystalline metallosilicate synthesized in the crystallization step (L represents alkali metal such as Na) is ion-exchanged with $NH_4$, thereby to produce $NH_4$-crystalline metallosilicate. This ion exchanging is conducted in such a manner that a L-crystalline metallosilicate is immersed in aqueous $NH_4$ solution.

As aqueous $NH_4$ solution used, there can be used aqueous ammonium salt solutions such as ammonium nitrate and ammonium chloride. When the concentration of $NH_4$ in the aqueous solution is too low, the ion-exchanging time will become long, whereas when the aqueous ammonium salt solution with high concentration is used, the ammonium salt not being ion-exchanged is wasted. Thus, the aqueous solution may be equivalence with the exchanging capacity of $NH_4$ to hundredfold equivalence, and the concentration of ammonium salt may be 0.01 to 5.0 mol/l. It is preferable that $NH_4$ is twofold equivalence to 30 times equivalence, and the concentration of ammonium salt is 0.05 to 2.0 mol/l.

The temperature of the aqueous ammonium salt solution in the ion-exchanging step may be above room temperature and also lower than 100° C. When the temperature of the aqueous ammonium salt solution is high, the ion-exchanging speed can be accelerated; it is not preferable because at 100° C. or more, the evaporation of water is fast, so a pressure-resistant container is required to suppress the evaporation of water. On the other hand, when the temperature of the aqueous ammonium salt solution is low, it is not preferable because the ion-exchanging speed will become low.

The immerstion time in the ion-exchanging step is 15 minutes to 6 hours, preferably 30 minutes to 2 hours. When the time is short, the exchange of L atoms in a metallosilicate is not completed, whereas when the time is long, the ion-exchange cannot be promoted any more than a certain level due to the ion-exchange equilibrium.

The present ion-exchanging step is conducted by immersing the L— crystalline metallosilicate into the aqueous ammonium salt solution; it is preferable that, while suppressing the block of the ion-exchange due to the equilibrium to replace L atoms in the crystalline metallosilicate with $NH_4$ efficiently, the combination of the immersion and the replacement of the aqueous ammonium salt solution is conducted repeatedly.

Additionally, the second production method in the present embodiment is to ion-exchange L atoms in the L— crystalline metallosilicate for $NH_4$, and it is possible to replace L atoms in the L— crystalline metallosilicate by H atoms using an aqueous mineral acid solution such as hydrochloric acid and nitric acid. In this case, it is suitable that conditions such as the concentration of mineral acid and the temperature of the aqueous solution is to be the same as in the ion-exchange using the foregoing ammonium salt. Regarding the concentration of mineral acid, when it is high, the metallosilicate is sometimes destroyed, as well as mineral acids which are not to be ion-exchanged are wasted.

In the burning step as the final step, a $NH_4$— crystalline metallosilicate produced in the ion-exchanging step is converted to a H— crystalline metallosilicate. Being associated with this conversion, the residual organic substances in the metallosilicate are burned out.

The burning step is suitably conducted under air stream. When the buring temperature is too low, there are some instances that certain organic substances and $NH_4$ remain, whereas when the burning temperature is too high, the metallosilicate crystal is sometimes destroyed, so the burning temperature is suitably 350 to 600° C. Further, when the buring time is too short, there are some instances that certain organic substances and $NH_4$ remain, whereas when the burning time is too long, there are some instances that the metallosilicate crystal is destroyed, so the burning time is suitably 2 to 10 hours.

The second production method is as described above. The catalyst produced according to the second production method has a degree of the crystallization of 85% or more. Further, in the catalyst produced by the second production method, the content of heteroatoms outside of MFI crystal lattices is 3% by mass or less relative to the total amount of T atoms inside of MFI crystal lattices and heteroatoms outside of MFI crystal lattices.

The above-described second production method is to produce the metallosilicate MFI structure, in order to produce the catalyst composed of crystalline metallosilicates other than MFI, the catalyst may be suitably produced by using known methods disclosed in Japanese Unexamined Patent Publication Nos. 2001-180928, 2001-139324 or 2001-114512. When the catalyst is produced by the known method, the mode diameter can be adjusted suitably by setting the drying time in the carrying step.

Next, the production method of the catalyst in the present embodiments will be described on the basis of the third methods. The third method is a method that M atoms is added to crystalline metallosilicates satisfying L/T<0.3.

As the preparation method of the crystalline metallosilicates, known preparation methods are listed. For example, it can be synthesized by hydrothermal synthesis method, dry-gel conversion method, or solid phase crystallization method. The above first and second production methods may also be used. L atoms are added as alkali raw material to a raw material solution or a raw material slurry in the preparation process of the crystalline metallosilicate, usually are contained in the crystalline metallosilicate prepared.

For example, as method for producing ZSM-5 of the crystalline metallosilicate, there can be listed the hydrothermal synthesis method described in the specification of U.S. Pat. No. 3,702,886, the dry-gel conversion method described in the specification of Japanese Unexamined Patent Publication No. 2000-344515, and the solid phase crystallization method described in the specification of Japanese Unexamined Patent Publication No. 2001-058817.

To replace exchangeable L atoms outside of the crystalline metallosilicate lattices by protons, normally, the L atoms are suitably ion-exchanged, for instance, with ammonium ions, and heat-treated at a high temperature. To prepare the crystalline metallosilicates of which L/T is less than 0.3, the number of times of the above ion-exchange and heat treatment is suitable to be one or more.

The L/T is suitably L/T<~0.2, preferably L/T<0.1, more preferably L/T<0.05, further preferably L/T<0.01, and the best is that almost all of L atoms are replaced with protons.

The M atoms added to crystalline metallosilicates are alkali metal atom such as Li, Na, K, Rb and Cs; alkaline earth metal atom such as Be, Mg, Ca, Sr and Ba; and rare earth metal atom such as Sc, Y, La, Ce, Pr, Nd, Sm, Gd, Dy and Ho. M atoms to be added may be one kind or, two kinds or more, when two kinds or more are added, they may be mixed and added. M atoms to be added are not limited, it is preferably Li, Na, K, Rb, Cs, Ca, Sr, Ba, Y, La or Ce, more preferably Na, K, Rb, Cs, Ba, or Y.

The content of M atoms in the crystalline metallosilicates is to be considered in conjunction with the amount of L atoms.

The preferable ratio of T atoms, L atoms, and M atoms is 0<(L+M)/T<1.0, more preferably 0<(L+M)/T<0.8, and most preferably 0<(L+M)/T<0.5.

The method of adding M atoms to crystalline metallosilicates is not particularly limited; ordinary methods can be adopted. Examples of the method include, but are not limited to carrying method by kneading method, impregnation method, and ion-exchanging method. A source compound of M atoms being added to crystalline metallosilicates is adequately selected from the compound having physical properties such as specific water solubility, required for the catalyst preparation. For example, M atom-containing inorganic salt such as chloride, fluoride, bromide, iodide, sulfide, nitride, hydroxide, oxide, nitrate, sulfate, carbonate and phosphate; M atom-containing organic salt such as alkoxide, acetate and propionate are listed; particularly nitrate and carbonate are suitable.

The M atoms contained in crystalline metallosilicates are generally in ions or oxides. These M ions and M oxides have suppressing effects on coking of the catalyst, being capable of suppressing the deterioration of the catalyst reactivity, if necessary, M ions or M oxides may be heat-treated under air stream. Namely, the burning of crystalline metallosilicates containing M atom may be conducted. For example, the burning of crystalline metallosilicate can be conducted under air stream in a rang of room temperature to 600° C. The temperature range of the burning must be limited in a range where the crystal structure of crystalline metallosilicate, is not to be destroyed. When the crystal structure of crystalline metallosilicate is destroyed, T atom is disengaged outside the lattice (in the case where T atom is Al atom, Al atom is disengaged outside the lattice of crystalline aluminosilicate), this disengagement may cause a significant decline of the yield of acrolein.

In production of acrolein, it is preferable to choose gas phase dehydration reaction where the glycerin-containing gas and the catalyst are contacted in any one of the reactor selected from the group of a fixed bed reactor, a moving bed reactor or the like. Additionally, the production method of acrolein of the present invention is not limited to the gas phase dehydration reaction where the glycerin-containing gas and the catalyst are contacted, may be a liquid phase dehydration reaction where the glycerin solution and the catalyst are contacted.

Glycerin used in the glycerin-containing gas may be either purified glycerin or crude glycerin. The concentration of glycerin in the glycerin-containing gas is not particularly limited, suitably 0.1 to 100 mol %, preferably 1 mol % or more, 10 mol % or more being capable of generating acrolein economically and highly efficiently is preferred. Additionally, in the case where the adjustment of the glycerin concentration is necessary in the glycerin-containing gas, one or more kinds of gases selected from the group of water vapor, nitrogen and air etc as concentration adjusting gases can be used. Further, when water vapor is contained in the glycerin-containing gas, it is preferable because yield of acrolein is increased as well as the lowering of the activities of the dehydration of the catalyst is suppressed.

The amount of the glycerin-containing gas in a reactor is suitably 100 to 10000 $hr^{-1}$ as expressed in flow rate of the glycerin-containing gas per unit catalyst volume (GHSV). It is preferably 5000 $hr^{-1}$ or less, more preferably 3000 $hr^{-1}$ or less to conduct the production of acrolein economically and highly efficiently. Further, the temperature to promote an intramolecular dehydration reaction of glycerin is suitably 200 to 500° C., preferably 250 to 450° C., and further preferably 300 to 400° C. Moreover, the pressure in the dehydration reaction is not particularly limited as long as the pressure is in a certain range where glycerin is not condensed. Generally, it is suitably 0.001 to 1 MPa, preferably 0.01 to 0.5 MPa.

Acrolein can be produced by the above method. Acrolein which has been produced, as is already known, can be used for a raw material of the production in acrolein derivative such as acrylic acid, 1,3-propanediol, acryl alcohol, polyacrylic acid, polyacrylate, methionine, 3-methylpropionaldehyde. Hence, the production method of acrolein can be obviously incorporated in the production methods of acrolein derivatives.

EXAMPLES

The present invention will be specifically described below with reference to Examples, the present invention is not limited to the following examples, is suitably modified within the scope conforming to the object described previously and below, and can be conducted, those are included within the technical scope of the present invention.

Acrolein was produced using catalysts. The detail preparation methods of catalysts used in respective Examples and Comparative examples, and the production method of acrolein are as follows.

Example 1

A catalyst was prepared according to the following carrying step, crystallization step and ion-exchanging step.

Carrying Step 0.58 g of NaOH and 1.95 g of $NaAlO_2$ ($NaAlO_2$ manufactured by Asada Chemical Industry Co., Ltd, $NaAlO_2$ content: 86.8 mass %) were sequentially dissolved in 15.00 g of distilled water, further 10.15 g of 40 mass % tetra-n-propylammonium hydroxide aqueous solution was added to the distilled water. Then, to this solution, distilled water was added to prepare an impregnation liquid such that the total amount was 30 ml. Next, as a silica compact, silica bead ("Cariact Q-50", 10 to 20 mesh, average pore diameter of 50 nm, manufactured by Fuji Silysia Chemical Ltd.) was used, into 30 g of silica bead dried at 120° C. for one day, the impregnation liquid was impregnated for one hour. Thereafter, the silica bead was dried in an evaporating dish placed over a hot water bath at 100° C., then further dried at 80° C. under nitrogen stream for 5 hours, Na/Al crystallizing agent necessary for crystallization was carried in the silica bead, thereby to give a crystalline metallosilicate precursor.

Crystallization Step

The precursor obtained in the carrying step was placed in a crucible made of tetrafluoroethylene, excluding the bottom part thereof, of 100 ml volume equipped with a jacket, 1.00 g of distilled water was introduced into the bottom of the crucible, this crucible was allowed to stand in an electric-furnace at 180° C. for 8 hours.

Ion-Exchanging Step

The solid material obtained by the operation of the crystallization step was immersed in 300 g of one mol/l aqueous ammonium nitrate solution at 60° C., stirred for 1 hour, and then the supernatant liquid was discarded. The operation of from the immersion to the discard was repeated plural times. Thereafter, the solid material was washed with water.

Burning Step

The solid material after the ion-exchanging step was burned in air stream at 540° C. for 3.5 hours. A H-MFI catalyst was obtained by this burning.

Example 2

Crystalline metallosilicate powders (a NH$_4$-MFI, "5524G", T atom: Al manufactured by ZEOLYST International) were pressure-formed, then crushed coarsely, and classified. This classified crystalline metallosilicate powders in the range of 0.7 to 2.0 mm was placed in air stream and burned at 540° C. for 3 hours, thereby to be obtained a H-MFI catalyst.

Examples 3 to 6

A H-MFI catalyst was obtained in the same manner as in Example 1 except that in the carrying step, the amounts of NaOH and NaAlO$_2$ used were changed. The amounts of NaOH and NaAlO$_2$ used in respective Examples were set to be as followed: 1.29 g of NaOH and 0.67 g of NaAlO$_2$ for Example 3; 1.40 g of NaOH and 0.47 g of NaAlO$_2$ for Example 4; 1.53 g of NaOH and 0.23 g of NaAlO$_2$ for Example 5; and 1.61 g of NaOH and 0.094 g of NaAlO$_2$ for Example 6.

Example 7

A H-BEA catalyst was obtained in the same manner as in Example 2 except that as a crystalline metallosilicate powder, a NH$_4$-BEA ("CP814E", T atom: Al, manufactured by ZEOLYST International) was used.

Example 8

H-MFI catalyst was obtained in the same manner as in Example 1 except that in the carrying step: 1.65 g of NaOH was used, 10.14 g of 40 mass % tetra-n-propylammonium hydroxide aqueous solution was used, and 2.01 g of Fe(NO$_3$)$_3$.9H$_2$O was used in place of NaAlO$_2$.

Example 9

A H-MFI catalyst was obtained in the same manner as in Example 1 except that in the carrying step: 1.65 g of NaOH was used, 10.14 g of 40 mass % tetra-n-propylammonium hydroxide aqueous solution was used, and 2.10 g of Ga(NO$_3$)$_3$.9H$_2$O was used in place of NaAlO$_2$.

Comparative Example 1

H-MFI catalyst was obtained in the same manner as in Example 1 except that in the carrying step: 1.64 g of NaOH was used, 0.047 g of NaAlO$_2$ was used, and drying at 80° C. under nitrogen stream was conducted for 7 hours.

Comparative Example 2

H-MFI catalyst was obtained in the same manner as in Comparative example 1 except that in the carrying step drying under nitrogen stream was conducted for 0.5 hours; and in the ion-exchanging step, the operation numbers of times in the immersion into aqueous ammonium nitrate and the discard of supernatant liquid were reduced to less than those in Comparative example 1.

Comparative Example 3

A H-MFI catalyst was obtained in the same manner as in Comparative example 2 except that in the carrying step, drying under nitrogen stream was conducted for 5 hours; and in the ion-exchanging step, the operation numbers of times in the immersion into aqueous ammonium nitrate and the discard of supernatant liquid were reduced to less than those in Comparative example 2.

Comparative Example 4

H-MFI catalyst was obtained in the same manner as in Example 1 except that in the carrying step: 1.99 g of NaOH was used, 0.0094 g of NaAlO$_2$ was used, and 16.92 g of 40 mass % of tetra-n-propylammonium hydroxide aqueous solution was used.

Comparative Example 5

70 g of NH$_4$-MFI powders ("CBV5524G", T atom: Al, manufactured by ZEOLYST International Corporation) and 30 g of silica as binder were dispersed in the ion-exchanging water, then concentrated until to be in paste. Solid material obtained by drying this concentrate at 110° C., was burned at 500° C. for 5 hours, crushed coarsely, then classified in the range of 0.7 to 2.0 mm, thereby to give a H-MFI catalyst.

Comparative Examples 6 to 8

A commercially available metallosilicates compact that was formed using alpha-alumina as a binder was burned at 500° C. for 3 hours, crushed coarsely, then classified in the range of 0.7 to 2.0 mm, thereby to give a H-MFI catalyst. The commercially available metallosilicates used were as follows: a NH$_4$-MFI ("CBV5524GCY", T atom: Al, manufactured by ZEOLYST International Corporation) for Comparative example 6; a NH$_4$-MFI ("SN486H/99", T atom: Al, manufactured by SUD-CHEMIE Performance Packing) for Comparative example 7; and a NH$_4$-MFI ("CBV3024ECY", T atom: Al, manufactured by ZEOLYST International Corporation) for Comparative example 8. Further, the mass ratio of "crystalline metallosilicate"/"binder" in respective metallosilicates compacts used is 70/30.

The preparation methods of catalysts used in Examples 1 to 9, and Comparative examples 1 to 8 are as described above. Si/T ratios of these catalysts and Na contents in terms of Na$_2$O in the catalysts were calculated. For the calculated, analytical values were adopted using a fluorescent X-ray analyzer ("PW2404" manufactured by PHILPS Corporation, detection limit of Na$_2$O: 75 ppm).

Production of Acrolein

Acrolein was synthesized by dehydrating glycerin in the following method using a fixed bed reactor which was putted a catalyst. A stainless steel reacting tube of 10 mm in inner diameter and 500 mm in length being filled with 15 ml of a catalyst, then this reactor was immersed in a salt bath at 360° C. Thereafter, nitrogen was poured into the reactor for 30 minutes at a flow rate of 62 ml/min, then the glycerin-containing gas (the composition of the glycerin-containing gas: glycerin 27 mol %, water 34 mol %, nitrogen 39 mol %) was poured at a flow rate of 632 hr$^{-1}$. For 30 minutes after passage of a certain time from the glycerin-containing gas poured in the reactor, the gas flown out from the reactor was absorbed in acrylonitrile, glycerin and acrolein in the acrylonitrile were analyzed. This analysis employed a gas chromatography(GC) equipped with FID as a detector, the internal standard method was adopted.

In a qualitative analysis with the GC, glycerin, acrolein and 1-hydroxyacetone were detected.

The conversion rate of glycerin (hereinafter simply called "the conversion rate") and the yield of acrolein (hereinafter simply called "the yield") were calculated from the above results of quantitative analysis with the GC. The rate of change in the yield of acrolein (hereinafter simply called "the rate of change") was also calculated. The calculation formulas for the conversion rate and the yield was the following formula (1) and formula (2):

$$\text{Conversion rate (\%)} = \left(1 - \frac{\text{Amount of glycerin absorbed in acrylonitrile (mol)}}{\text{Amount of glycerin flown into reactor for 30 minutes (mol)}}\right) \times 100 \quad \text{Formula (1)}$$

$$\text{Yield(\%)} = \frac{\text{Amount of acrolein absorbed in acrylonitrile(mol)}}{\text{Amount of glycerin flown into reactor for 30 minutes (mol)}} \times 100 \quad \text{Formula (2)}$$

Table 1 shows the results on the foregoing Si/T, content of Na$_2$O, conversion rate, yield, and rate of change.

In Table 1, the following can be confirmed when Examples 1 to 7 and Comparative examples 1 to 8 having Al as T atom in common are compared. The absolute values of the rate of changes in Comparative examples 1 and 2 where the catalysts having more than 800 of Si/T ratios were used are each as a large values as more than 33%. Either yield of acrolein in Comparative example 3 with Si/T of 1000 and Comparative example 4 with Si/T of 5000 is about 2%, thus they are not preferable production methods of acrolein. Further, the absolute values of the rate of changes in Comparative examples 5 to 8 where the catalysts having binder content of more than 15% by mass were used are each as a large as more than 26%. On the other hand, the absolute values of the rate of changes in Examples 1 to 7 where the catalysts having Si/T of 800 or less and the binder content of 15% by mass or less were used are each as a small as 12% or less. Hence, it can be confirmed that acrolein was produced while suppressing the rate of changes in Examples 1 to 7.

In the same manner as Examples 1 to 9 and Comparative examples 1 to 8, the production of acrolein was conducted for the following Examples 10 to 15 and Comparative examples 9 to 12. Si/T ratio and the content of Na in terms of Na$_2$O in the catalyst used in the examples were calculated. The mode diameter on volume basis of the catalyst was also measured for the catalysts of Examples 10 to 15 and Comparative examples 9 to 12. The detailed descriptions for the prepara-

TABLE 1

| | CMS | Si/T | T | Binder Kind | Binder Content percentage (%) | Na$_2$O (wt. %) | Flowing time (min) | Conversion rate (%) | Yield (mol %) | Rate of change (%) |
|---|---|---|---|---|---|---|---|---|---|---|
| Example 1 | MFI | 24 | Al | — | — | ND | 30 | 99.0 | 61.0 | −4.3 |
| | | | | | | | 150 | 96.4 | 58.4 | |
| Example 2 | MFI | 28 | Al | — | — | ND | 30 | 99.7 | 71.2 | −11.2 |
| | | | | | | | 150 | 91.7 | 63.2 | |
| Example 3 | MFI | 70 | Al | — | — | ND | 30 | 99.8 | 64.2 | +7.8 |
| | | | | | | | 150 | 99.6 | 69.2 | |
| Example 4 | MFI | 100 | Al | — | — | ND | 30 | 99.9 | 62.3 | +6.7 |
| | | | | | | | 150 | 99.8 | 66.5 | |
| Example 5 | MFI | 200 | Al | — | — | ND | 30 | 100 | 61.0 | 0.0 |
| | | | | | | | 150 | 100 | 61.0 | |
| Example 6 | MFI | 500 | Al | — | — | ND | 30 | 100 | 55.4 | +6.7 |
| | | | | | | | 150 | 99.1 | 51.7 | |
| Example 7 | BEA | 12.5 | Al | — | — | 0.050 | 30 | 99.9 | 36.1 | −3.9 |
| | | | | | | | 150 | 98.3 | 34.7 | |
| Example 8 | MFI | 100 | Fe | — | — | ND | 30 | 97.7 | 43.3 | −39.0 |
| | | | | | | | 150 | 86.6 | 26.4 | |
| Example 9 | MFI | 100 | Ga | — | — | ND | 30 | 96.2 | 59.4 | −9.6 |
| | | | | | | | 150 | 95.5 | 65.1 | |
| Comparative example 1 | MFI | 1000 | Al | — | — | ND | 30 | 98.3 | 46.2 | −33.5 |
| | | | | | | | 150 | 88.3 | 30.7 | |
| Comparative example 2 | MFI | 1000 | Al | — | — | 0.047 | 30 | 69.9 | 29.3 | −43.7 |
| | | | | | | | 150 | 51.0 | 16.5 | |
| Comparative example 3 | MFI | 1000 | Al | — | — | 1.173 | 30 | 58.3 | 2.5 | −16.0 |
| | | | | | | | 150 | 52.9 | 2.1 | |
| Comparative example 4 | MFI | 5000 | Al | — | — | 0.016 | 30 | 26.5 | 2.1 | −28.6 |
| | | | | | | | 150 | 23.8 | 1.5 | |
| Comparative example 5 | MFI | 28 | Al | Silica | 30 | ND | 30 | 100 | 61.5 | −26.7 |
| | | | | | | | 150 | 92.4 | 45.1 | |
| Comparative example 6 | MFI | 28 | Al | α-alumina | 30 | ND | 30 | 100 | 30.3 | +41.9 |
| | | | | | | | 150 | 97.8 | 43.0 | |
| Comparative example 7 | MFI | 12.5 | Al | α-alumina | 30 | ND | 30 | 98.3 | 7.6 | +447.4 |
| | | | | | | | 150 | 98.2 | 41.6 | |
| Comparative example 8 | MFI | 15 | Al | α-alumina | 30 | ND | 30 | 97.4 | 27.8 | +56.1 |
| | | | | | | | 150 | 95.4 | 43.4 | |

CMS: crystalline metallosilicate, Flowing time: accumulated flowing time of glycerin containing gas
Conversion rate: conversion rate of glycerin, Yield: yield of acrolein
Rate of change: rate of change based on the yield of acrolein in flowing time of 30 to 60 min, ND: not detected tion methods of each catalyst and the measurements of mode diameters on volume basis are as follows:

Examples 10 to 15

In the catalyst preparation of Example 12, the drying time under nitrogen stream at 80° C. in the carrying step in Example 1 was changed to 7 hours. In the preparation of a H-MFI catalyst used in Examples 10 to 15, the amounts of NaOH and Na$_2$O used in the carrying step in Example 1 were changed as well. The catalysts used in Examples 10 to 15 were prepared in the same manner as in Example 1 except for the above change. The amounts of NaOH and NaAlO$_2$ used in respective Examples were set to be as followed: 0.58 g of NaOH and 1.95 g of NaAlO$_2$ for Example 10; 1.29 g of NaOH and 0.67 g of NaAlO$_2$ for Example 11; 1.40 g of NaOH and 0.47 g of NaAlO$_2$ for Example 12; 1.40 g of NaOH and 0.47 g of NaAlO$_2$ for Example 13, 1.53 g of NaOH and 0.23 g of NaAlO$_2$ for Example 14, and 1.61 g of NaOH and 0.094 g of NaAlO$_2$ for Example 15.

Comparative Example 9

A H-MFI catalyst was obtained in the same manner as in Example 1 except that in the carrying step: 1.64 g of NaOH was used, 0.047 g of NaAlO$_2$ was used, and the drying at 80° C. under nitrogen stream was conducted for 7 hours.

Comparative Example 10

A H-MFI-catalyst was obtained in the same manner as in Comparative example 9 except that in the ion-exchanging step, the operation numbers of times in the immersion into aqueous ammonium nitrate and the discard of supernatant liquid were reduced to less than those in comparative example 9.

Comparative Example 11

A H-MFI catalyst was obtained in the same manner as in Comparative example 9 except that in the carrying step drying at 80° C. under nitrogen stream was conducted for 3 hours; and in the ion-exchanging step, the operation numbers of times in the immersion into aqueous ammonium nitrate and the discard of supernatant liquid-were reduced to less than those in Comparative example 10.

Comparative Example 12

A H-MFI catalyst was obtained in the same manner as in Comparative example 9 except that in the carrying step: drying at 80° C. under nitrogen stream was conducted for 0.5 hours; and in the ion-exchanging step, the operation numbers of times in the immersion into aqueous ammonium nitrate and the discard of supernatant liquid were reduced to less than those in Comparative example 9.

Measurement of Mode Diameter

It was measured by a mercury injection method using a porosimeter ("Autopore 9420III", manufactured by Shimadzu, Corporation). The measuring conditions were set to: a measuring pressure of 1 to 60000 psia, the contact angle of 130°, the surface tension of mercury of 485.0 mN/m, and the density of mercury of 13.5335 g/cm$^3$.

Table 2 shows the results on the foregoing Si/T ratios, the mode diameters, the contents of Na$_2$O, the conversion rate, the yields and the rates of change.

TABLE 2

| | Si/T | Mode diameter (μm) | Na$_2$O (wt. %) | Flowing time (min) | Conversion rate (%) | Yield (mol %) | Rate of change (%) |
|---|---|---|---|---|---|---|---|
| Example 10 | 24 | 0.2 | ND | 30 | 99.0 | 61.0 | −4.3 |
| | | | | 150 | 96.4 | 58.4 | |
| Example 11 | 70 | 0.13 | ND | 30 | 99.8 | 64.2 | +7.8 |
| | | | | 150 | 99.6 | 69.2 | |
| Example 12 | 100 | 0.08 | ND | 30 | 99.9 | 62.4 | +8.2 |
| | | | | 150 | 99.8 | 67.5 | |
| Example 13 | 100 | 0.15 | ND | 30 | 99.9 | 62.3 | +6.7 |
| | | | | 150 | 99.8 | 66.5 | |
| Example 14 | 200 | 0.1 | ND | 30 | 100 | 61.0 | 0 |
| | | | | 150 | 100 | 61.0 | |
| Example 15 | 500 | 0.1 | ND | 30 | 100 | 55.4 | −6.7 |
| | | | | 150 | 99.1 | 51.7 | |
| Comparative example 9 | 1000 | 0.06 | ND | 30 | 98.3 | 46.2 | −33.5 |
| | | | | 150 | 88.3 | 30.7 | |
| Comparative example 10 | 1000 | 0.15 | 0.018 | 30 | 88.1 | 45.0 | −40.7 |
| | | | | 150 | 67.0 | 26.7 | |
| Comparative example 11 | 1000 | 0.5 | 0.027 | 30 | 87.8 | 43.9 | −39.4 |
| | | | | 150 | 64.6 | 26.6 | |
| Comparative example 12 | 1000 | 0.9 | 0.047 | 30 | 69.9 | 29.3 | −43.7 |
| | | | | 150 | 51.0 | 16.5 | |

T: Al, Flowing time: accumulated flowing time of glycerine containing gas

Conversion rate: conversion rate of glycerin, Yield: yield of acrolein

Rate of change: rate of change based on the yield of acrolein in flowing time of 30 to 60 min,
ND: not detected As shown in Table 2, the yield of acrolein in Examples having a mode diameter of 0.80 or less and Si/T of 800 or less is higher than those in Comparative examples.

As Examples 16 to 27, acrolein was produced in the same manner as in the above Example 1 except that flow rate of the glycerin containing gas of 80% by mass was set to 650 hr$^{-1}$. The detailed preparation method of each catalyst used in the production is as follows. Additionally, L/T in the catalysts of Examples 16 to 27 adopted the values calculated from the analytical values by a fluorescent X-ray analyzer ("PW2404" manufactured by PHILPS Corporation, detection limit of Na$_2$O: 75 ppm). M/T values were also calculated by the following formula:

$$M/T \text{ in Examples 16 to 29} = \frac{\text{Mol amount of } M \text{ atoms in } M \text{ atom containing compound used for adding } M \text{ atoms}}{\text{Mol amount of } MFI \text{ before addition of } M \text{ atoms}}$$

Amount of $MFI$ before addition of $M$ atoms =

$$\frac{\text{Mass amount of } MFI \text{ before addition of } M \text{ atoms (g)}}{(\text{Molar weight of SiO}_2) \times \text{Si}/T + (\text{Molar weight of TiO}_2) + (\text{Atomic weight of } L \text{ atom}) \times L/T}$$

Example 16

A H-MFI catalyst was obtained in the same manner as in Example 1 except that in the carrying step 1.40 g of NaOH was used, 0.47 g of NaAlO$_2$ was used, and the drying time at 80° C. was 7 hours; and in the burning step, a solid material after the ion-exchanging step was burned at 550° C. for 5 hours. This MFI was immersed in 300 g of 1 mol/l ammonium nitrate aqueous solution at 60° C. and stirred for 1 hour, followed by discarding supernatant. The operation of from the immersion to the discard was repeated more than once, and the MFI was washed with water. Thereafter, A H-MFI catalyst was obtained by burning the MFI at 550° C. for 5 hours. The analytical value of Si/T of the catalyst used in Example 16 was 100. Additionally, Na$_2$O was not detected and L/T was zero.

Example 17

A H-MFI catalyst was obtained in the same manner as in Example 1 except that in the carrying step 1.40 g of NaOH was used, 0.47 g of NaAlO$_2$ was used, and the drying time at 80° C. was 7 hours; and in the burning step, a solid material after the ion-exchanging step was burned at 550° C. for 5 hours. The Si/T ratio of the catalyst was 100. Additionally, the analytical value of Na$_2$O was 0.43% by mass and L/T was 0.84.

Example 18

A MFI, having Si/T of 100, the analytical value of Na$_2$O of 0.036% by mass and L/T of 0.07, was prepared in the same manner as the catalyst in Comparative example 1. Further, 0.11 g of LiNO$_3$ and 27.98 g of distilled water were mixed to prepare a Li containing solution. Then, while stirring and mixing 40.0 g of the MFI prepared, the Li containing solution was added thereto, allowed to stand for 3 hours. Next, in an evaporating dish placed over a water bath at 90° C., the resultant mixture was dried while stirring the MFI. The MFI after drying was placed in air stream at 120° C. for 9 hours, then burned under air stream at 550° C. for 5 hours. By adding M atom to the MFI through the operation from the addition of a Li containing liquid to the burning, the catalyst used in Example 18 was obtained. The calculated M/T of the catalyst was 0.24.

Examples 19 to 27

The catalysts used in Examples 19 to 27 were prepared in the same manner as in Example 18 except that the Li containing liquid was replaced with other liquids. The liquids used in place of the Li containing liquid were: a Na containing liquid prepared by mixing 0.02 g of Na$_2$CO$_3$ and 27.99 g of distilled water for Example 19; a Na containing liquid prepared by mixing 0.21 g of Na$_2$CO$_3$ and 27.92 g of distilled water for Example 20; a K containing solution prepared by mixing 0.029 g of K$_2$CO$_3$ and 27.99 g of distilled water for Example 21; a Rb containing solution prepared by mixing 0.049 g of Rb$_2$CO$_3$ and 27.97 g of distilled water for Example 22; a Cs containing solution prepared by mixing 0.041 g of Cs$_2$CO$_3$ and 27.96 g of distilled water for Example 23; a Cs containing solution prepared by mixing 0.462 g of Cs$_2$CO$_3$ and 27.72 g of distilled water for Example 24; a Cs containing solution prepared by mixing 0.660 g of Cs$_2$CO$_3$ and 27.34 g of distilled water for Example 25; an Y containing solution prepared by mixing 0.063 g of Y$_2$(CO$_3$)$_3$ and 27.97 g of distilled water for Example ~26; and a Ba containing solution prepared by mixing 0.205 g of Ba(NO$_3$)$_2$ and 27.92 g of distilled water for Example 27.

Further, the calculated M/T ratios of the catalysts in Examples 19 to 27 were as follows: 0.06 for Example 19; 0.60 for Example 20; 0.06 for Example 21; 0.07 for Example 22; 0.04 for Example 23; 0.43 for Example 24; 0.61 for Example 25; 0.05 for Example 26; and 0.12 for Example 27.

Measurement of the Amount of Coke Adhesion

After production of acrolein, nitrogen was circulated into the reactor at a flow rate of 62 ml/min for 30 minutes, then catalyst was picked out from the reactor. The amount of coke adhered on this catalyst was measured using a TG-DTA ("DTG-50H" manufactured by Shimadzu Corporation). The condition of this measurement was set in such a way that the amount of the specimen was 15 mg, the air flow rate was 50 ml/min, and after heating from room temperature to 900° C. at 10° C./min, then the temperature of 900° C. was maintained for 10 minutes. Additionally, the amount of coke adhered on the catalyst was expressed as a percentage of mass reduction of the catalyst in the foregoing condition.

Measurement of the Burning Temperature of Coke

In the above measurement of the amount of coke adhesion, the exothermic peak temperature of the catalyst specimen measured is defined as the burning temperature of coke.

Table 3 shows the results of Examples 16 to 27.

Additionally, each difference in a column "Amount of coke" in Table 3 is a difference from the amount of coke adhesion in Example 16 as a standard, which is calculated in the following formula. Further, each difference in a column "Burning temperature of coke" in Table 3 is a temperature difference from $$\text{Difference in amount of coke (\%)} = \frac{\begin{pmatrix}\text{Amount of coke}\\\text{adhesion(\%)}\\\text{in respective}\\\text{Examples 17}\\\text{to 27}\end{pmatrix} - \begin{pmatrix}\text{Amount of coke}\\\text{adhesion (\%)}\\\text{in Example 16}\end{pmatrix}}{\text{Amount of coke}\\\text{adhesion (\%)}\\\text{in Example 16}} \times 100$$

the measurement in Example 16 as a standard.

acrolein is largely lowered in the case of large amount of Na as L atom.

Productions of acrolein in Examples 28 and 29 were conducted in the same manner as in Examples 16 to 27. The details of the production methods of the respective catalysts in Examples 28 and 29 were as follows.

Example 28

A H-MFI catalyst was obtained in the same manner as in Example 1 except that in the carrying step 1.40 g of NaOH was used, 1.74 g of $Ga(NO_3)_3$ $9H_2O$ was used in place of $NaAlO_2$, and the drying time at 80° C. was 7 hours; and in the

TABLE 3

| | Before addition of M atom | | | After addition of M atom | | | Flowing time (hr) | Conversion rate (%) | Yield (%) | Rate of change (%) | Amount of coke Amount of adhesion (wt. %) | Differ-ence (%) | Burning temperature of coke Measurement (° C.) | Differ-ence (° C.) |
|---|---|---|---|---|---|---|---|---|---|---|---|---|---|---|
| | Si/T | Na₂O (wt. %) | L/T | M atom | M/T | (L + M)/T | | | | | | | | |
| Example 16 | 100 | ND | 0.00 | — | 0.00 | 0.00 | 0.5 | 100 | 62.7 | — | 8.5 | 0 | 530 | 0 |
| | | | | | | | 2.5 | 100 | 65.8 | +4.9 | | | | |
| | | | | | | | 4.5 | 100 | 66.1 | +5.4 | | | | |
| Example 17 | 100 | 0.43 | 0.84 | — | 0.00 | 0.84 | 0.5 | 82.2 | 6.3 | — | 6.7 | −21.2 | — | — |
| | | | | | | | 2.5 | 24.1 | 4.8 | −23.8 | | | | |
| Example 18 | 100 | 0.036 | 0.07 | Li | 0.24 | 0.31 | 0.5 | 100 | 66.7 | — | 7.9 | −7.1 | 526 | −4 |
| | | | | | | | 2.5 | 100 | 68.1 | +2.1 | | | | |
| | | | | | | | 4.5 | 100 | 65.2 | −2.2 | | | | |
| Example 19 | 100 | ND | 0.00 | Na | 0.06 | 0.06 | 0.5 | 100 | 63.5 | — | 8.6 | +1.2 | 520 | −10 |
| | | | | | | | 2.5 | 100 | 70.5 | +11.0 | | | | |
| | | | | | | | 4.5 | 100 | 68.3 | +7.6 | | | | |
| Example 20 | 100 | ND | 0.00 | Na | 0.60 | 0.60 | 0.5 | 100 | 58.3 | — | 3.6 | −57.6 | — | — |
| | | | | | | | 2.5 | 93.5 | 47.7 | −18.2 | | | | |
| Example 21 | 100 | ND | 0.00 | K | 0.06 | 0.06 | 0.5 | 100 | 64.6 | — | 8.1 | −4.2 | 524 | −6 |
| | | | | | | | 2.5 | 100 | 69.2 | +7.1 | | | | |
| | | | | | | | 4.5 | 100 | 65.6 | +1.5 | | | | |
| Example 22 | 100 | ND | 0.00 | Rb | 0.07 | 0.07 | 0.5 | 100 | 65.3 | — | 8.4 | −1.2 | 520 | −10 |
| | | | | | | | 2.5 | 100 | 69.6 | +6.6 | | | | |
| | | | | | | | 4.5 | 100 | 69.9 | +7.0 | | | | |
| Example 23 | 100 | ND | 0.00 | Cs | 0.04 | 0.04 | 0.5 | 100 | 62.2 | — | 8.0 | −5.9 | 528 | −2 |
| | | | | | | | 2.5 | 100 | 65.2 | +4.8 | | | | |
| | | | | | | | 4.5 | 100 | 68.7 | +10.5 | | | | |
| Example 24 | 100 | ND | 0.00 | Cs | 0.43 | 0.43 | 0.5 | 100 | 72.5 | — | 6.3 | −25.9 | 504 | −26 |
| | | | | | | | 2.5 | 100 | 74.2 | +2.3 | | | | |
| | | | | | | | 4.5 | 100 | 66.7 | −8.0 | | | | |
| Example 25 | 100 | 0.015 | 0.03 | Cs | 0.61 | 0.64 | 0.5 | 100 | 60.6 | — | 5.5 | −35 | 504 | −26 |
| | | | | | | | 2.5 | 100 | 61.0 | +0.7 | | | | |
| | | | | | | | 4.5 | 96.7 | 54.9 | −9.4 | | | | |
| Example 26 | 100 | 0.026 | 0.05 | Ba | 0.05 | 0.17 | 0.5 | 100 | 68.5 | — | 8.0 | −5.9 | 523 | −7 |
| | | | | | | | 2.5 | 100 | 79.0 | +15.3 | | | | |
| | | | | | | | 4.5 | 100 | 67.7 | −1.2 | | | | |
| Example 27 | 100 | ND | 0.00 | Y | 0.12 | 0.05 | 0.5 | 100 | 60.0 | — | 8.8 | +3.5 | 526 | −4 |
| | | | | | | | 2.5 | 100 | 63.8 | +6.3 | | | | |
| | | | | | | | 4.5 | 100 | 63.1 | +5.2 | | | | |

T: Al, Flowing time: accumulated flowing time of glycerin containing gas
Conversion rate: conversion rate of glycerin, Yield: yield of acrolein
Rate of change: rate of change based on the yield of acrolein in flowing time of 0.5 to 1 hr, ND: not detected As shown in Table 3, the catalysts that M atom was added in Examples 18 to 27 have a negative value in burning temperature difference from the standard of Example 16. This fact indicates a possibility that regeneration treatment of catalyst can be easily conducted by combusting removal of coke. Further, in comparison with Example 17 and Example 20 having same content of Na, it is known that the yield of burning step, a solid material after the ion-exchanging step was burned at 550° C. for 5 hours. This MFI was immersed in 300 g of 1 mol/l ammonium nitrate aqueous solution at 60° C. and stirred for 1 hour, followed by discarding supernatant. The operation of from the immersion to the discard was repeated more than once, and the MFI was washed with water. Thereafter, a H-MFI catalyst was obtained by burning the MFI at 550° C. for 5 hours. The Si/T ratio of the catalyst was 100. Additionally, Na$_2$O was not detected and L/T was zero.

Example 29

A MFI having 100 of Si/T and zero of L/T was prepared in the same manner as the catalyst in Example 28. Further, 0.02 g of Na$_2$CO$_3$ and 27.99 g of distilled water were mixed to prepare a Na containing solution. Then, while stirring and mixing 40.0 g of the MFI prepared, the Na containing solution was added thereto, allowed to stand for 3 hours. Next, in an evaporating dish placed over a water bath at 90° C., the resultant mixture was dried while stirring the MFI, the MFI after drying was placed in air stream at 120° C. for 9 hours, then burned under air stream at 550° C. for 5 hours. By adding M atom to the MFI through the operation from the addition of a Na containing liquid to the burning, the catalyst used in Example 29 was obtained. The calculated M/T of the catalyst was 0.06.

Table 4 shows the results of Examples 28 and 29.

Additionally, each difference in a column "Amount of coke" in Table 4 is a difference from the amount of coke adhesion in Example 28 as a standard, which is calculated in the following formula. Further, each difference in a column "Burning temperature of coke" in Table 4 is a temperature difference from the measurement in Example 28 as a standard.

$$\text{Difference in amount of coke (\%)} = \frac{\begin{pmatrix}\text{Amount of coke} \\ \text{adhesion (\%)} \\ \text{in Example 29}\end{pmatrix} - \begin{pmatrix}\text{Amount of coke} \\ \text{adhesion (\%)} \\ \text{in Example 28}\end{pmatrix}}{\begin{array}{c}\text{Amount of coke} \\ \text{adhesion (\%)} \\ \text{in Example 28}\end{array}}$$

cates is 800 or less, and glycerin is dehydrated by a gas phase reaction of contacting glycerin gas and the catalyst.

2. The method according to claim 1, wherein the catalyst has no binder.

3. The method according to claim 1, wherein the catalyst is a compact comprising the crystalline metallosilicates, and the compact has a mode diameter on volume basis of 0.80 μm or less measured by a mercury injection method.

4. The method according to claim 3, wherein the mode diameter on volume basis is 0.05 μm or more.

5. The method according to claim 1, wherein the catalyst is a compact comprising the crystalline metallosilicates, and the compact has a mode diameter on volume basis of 0.08 to 0.40 μm measured by a mercury injection method.

6. The method according to claim 1, wherein a content of Na in terms of Na$_2$O in the crystalline metallosilicates is 1.0% by mass or less.

7. The method according to claim 1, wherein a content of Na in terms of Na$_2$O in the crystalline metallosilicates is 0.010% by mass or less.

8. The method according to claim 1, wherein the crystalline metallosilicates has H$^{30}$ in cation outside its crystal lattices.

9. The method according to claim 1, wherein the T atoms is at least one kind selected from Al, Ga, and Fe.

10. The method according to claim 1, wherein the T atoms is Al.

11. The method according to claim 1, wherein any one of the crystalline metallosilicates have a crystal structure of MFI type.

12. The method according to claim 1, wherein the crystalline metallosilicates have L atoms being a cation outside its crystal lattices other than H derived from a raw material of crystalline metallosilicate synthesis, and has at least one kind M atom selected from alkali metal atom, alkaline earth metal atom and rare earth metal atom being added to crystalline metallosilictes with less than 0.3 in the ratio L/T of mole number of the L atoms to mole number of T atoms.

TABLE 4

| | Before addition of M atom | | | After addition of M atom | | | Flowing time | Conversion rate | Yield | Rate of change | Amount of coke | | Burning temperature of coke | |
|---|---|---|---|---|---|---|---|---|---|---|---|---|---|---|
| | Si/T | Na$_2$O (wt. %) | L/T | M atom | M/T | (L + M)/T | (hr) | (%) | (%) | (%) | Amount of adhesion (wt. %) | Difference (%) | Measurement (° C.) | Difference (° C.) |
| Example 28 | 100 | ND | 0.00 | — | 0.00 | 0.00 | 0.5 | 96.2 | 59.4 | — | 8.7 | 0 | 537 | 0 |
| | | | | | | | 2.5 | 95.5 | 65.1 | +9.6 | | | | |
| | | | | | | | 4.5 | 95.3 | 63.1 | +6.2 | | | | |
| Example 29 | 100 | ND | 0.00 | Na | 0.06 | 0.06 | 0.5 | 100 | 65.0 | — | 8.6 | −1.2 | 524 | −13 |
| | | | | | | | 2.5 | 98.3 | 65.7 | +1.1 | | | | |

T: Ga, Flowing tine: accumulated flowing time of glycerin containing gas
Conversion rate: conversion rate of glycerin, Yield: yield of acrolein
Rate of change: rate of change based on the yield of acrolein in flowing time of 0.5 to 1 hr, ND: not detected It is known from the results of Table 4 that the effect of adding M atom to a crystalline metallosilicate does not depend on the kind of T atom.

The invention claimed is:

1. A method of producing acrolein which comprises dehydrating glycerin under coexistence with a catalyst having crystalline metallosilicates containing at least one kind of T atoms, wherein an amount of a binder in the catalyst is 15% by mass or less, a Si/T mole ratio in the crystalline metallosili-

13. The method according to claim 12, wherein the mole number of the L atoms, the mole number of the M atom and the mole number of the T atoms satisfy 0<(L+M)/T<1.0.

14. The method according to claim 12, wherein the M atom is at least one kind selected from Li, Na, K, Rb, Cs, Ca, Sr, Ba, Y, La and Ce.

15. A method of producing an acrolein derivative, comprising the method of producing acrolein according to claim 1.

* * * * *